(12) United States Patent
Raad

(10) Patent No.: US 8,426,044 B2
(45) Date of Patent: Apr. 23, 2013

US008426044B2

(54) METHOD FOR IMPARTING ANTIMICROBIAL ACTIVITY TO A MEDICAL DEVICE

(75) Inventor: Issam Raad, Missouri City, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 13/257,886

(22) PCT Filed: Mar. 18, 2010

(86) PCT No.: PCT/US2010/027768
§ 371 (c)(1),
(2), (4) Date: Dec. 5, 2011

(87) PCT Pub. No.: WO2010/107977
PCT Pub. Date: Sep. 23, 2010

(65) Prior Publication Data
US 2012/0064372 A1    Mar. 15, 2012

Related U.S. Application Data

(60) Provisional application No. 61/161,876, filed on Mar. 20, 2009.

(51) Int. Cl.
*A61L 27/54* (2006.01)
*A61L 29/16* (2006.01)
*B05D 7/00* (2006.01)

(52) U.S. Cl.
USPC .......................... 428/704; 428/411.1; 427/2.1

(58) Field of Classification Search ........................ None
See application file for complete search history.

(56) References Cited

U.S. PATENT DOCUMENTS

| | | | |
|---|---|---|---|
| 4,107,121 A | 8/1978 | Stoy | 260/29.6 |
| 4,442,133 A | 4/1984 | Greco et al. | 427/2 |
| 4,895,566 A | 1/1990 | Lee | 604/266 |
| 4,917,686 A | 4/1990 | Bayston et al. | 604/265 |
| 4,952,419 A | 8/1990 | De Leon et al. | 427/2 |
| 5,013,306 A | 5/1991 | Solomon et al. | 604/265 |
| 5,217,493 A | 6/1993 | Raad et al. | 623/11 |
| 5,624,704 A * | 4/1997 | Darouiche et al. | 427/2.24 |
| 5,902,283 A | 5/1999 | Darouiche et al. | 604/265 |
| 7,651,661 B2 | 1/2010 | Raad et al. | 422/28 |
| 2003/0078242 A1 | 4/2003 | Raad et al. | 514/150 |
| 2003/0176436 A1 | 9/2003 | Ala et al. | 514/251 |
| 2005/0197634 A1 | 9/2005 | Raad et al. | 604/265 |
| 2005/0220837 A1 | 10/2005 | Disegi et al. | 424/423 |
| 2007/0154621 A1 | 7/2007 | Raad | 427/2.1 |
| 2008/0090847 A1 | 4/2008 | Moe et al. | 514/262.1 |

OTHER PUBLICATIONS

"National Nosocomial Infections Surveillance (NNIS) System report, data summary from Oct. 1986-Apr. 1998, issued Jun. 1998," *Am J Infect Control.*, 26(5):522-533, 1998.

Benezra et al., "Prospective study of infections in indwelling central venous catheters using quantitative blood cultures," *Am J Med.*, 85:495-498, 1988.

Chaiban et al., "A rapid method of impregnating endotracheal tubes and urinary catheters with gendine: a novel antiseptic agent," *J. Antimicrob. Chemother.*, 55(1):51-56, 2005.

Chatzinikolaou et al., "Antibiotic-coated hemodialysis catheters for the prevention of vascular catheter-related infections: a prospective, randomized study," *Am J Med.*, 115(5):352-357, 2003.

Costerton et al., "Bacterial biofilms in nature and disease," *Ann. Rev. Microbiol.*, 41:435-464, 1987.

Darouiche et al., "A comparison of two antimicrobial-impregnated central venous catheters. Catheter study group," *N Engl J Med.*, 340(1):1-8, 1999.

Darouiche et al., "Comparison of antimicrobial impregnation with tunneling of long-term central venous catheters: a randomized controlled trial," *Ann Surg.*, 242(2):193-200, 2005.

Falagas et al., "Rifampicin-impregnated central venous catheters: a meta-analysis of randomized controlled trials," *J Antimicrob Chemother.*, 59(3):359-369, 2007.

Gudlaugsson et al., "Attributable mortality of nosocomial candidemia, revisited," *Clin Infect Dis.*, 37:1172-1177, 2003.

Hanna et al., "Comparative in vitro efficacies and antimicrobial durabilities of novel antimicrobial central venous catheters," *Antimicrob. Agents Chemother.*, 50(10):3283-3288, 2006.

Hanna et al., "Long-term silicone central venous catheters impregnated with minocycline and rifampin decrease rates of catheter-related bloodstream infection in cancer patients: a prospective randomized clinical trial," *J Clin Oncol.*, 22(15):3163-3171, 2004.

Kuhn et al., "Antifungal susceptibility of candida biofilms: unique efficacy of amphotericin B lipid formulations and echinocandins," *Antimicrobial Agents and Chemotherapy*, 46: 1773-1780, 2002.

León et al., "Benefits of minocycline and rifampin-impregnated central venous catheters: a prospective, randomized, double-blind, controlled, multicenter trial," *Intensive Care Med*, 30:1891-1899, 2004.

Maki et al., "The risk of bloodstream infection in adults with different intravascular devices: a systematic review of 200 published prospective studies," *Mayo Clin Proc.*, 81(9):1159-1171, 2006.

Mermel et al., "Guidelines for the management of intravascular catheter-related infections," *Clin Infect Dis.*, 32(9):I249-1272, 2001.

Mermel, "Prevention of intravascular catheter-related infections," *Ann Intern Med.*, 132(5):391-402, 2000.

O'Grady et al., "Guidelines for the prevention of intravascular catheter-related infections," *The Hospital Infection Control Practices Advisory Committee, Centers for Disease Control and Prevention*, U.S. *Pediatrics*, 110(5):e51, 2002.

PCT International Preliminary Report on Patentability issued in International Application No. PCT/US2010/027768, mailed Oct. 31, 2011.

(Continued)

*Primary Examiner* — Suzanne Ziska
(74) *Attorney, Agent, or Firm* — Parker Highlander PLLC

(57) ABSTRACT

A method for imparting broad spectrum antimicrobial activity to a medical device. The medical device is sequentially contacted with a first antimicrobial component, such as an antiseptic, and thereafter with a second antimicrobial component, such as a mixture of antibiotics. The first component may be a guanidium compound, such as chlorhexidine. The second component may be a mixture of a tetracycline, such as minocycline, and a rifamycin, such as rifampin.

11 Claims, 5 Drawing Sheets

OTHER PUBLICATIONS

PCT International Search Report and Written Opinion issued in International Application No. PCT/US2010/027768, mailed Jan. 31, 2011.

Raad et al., "Anti-adherence activity and antimicrobial durability of anti-infective-coated catheters against multidrug resistant bacteria," *J. Antimicrob. Chemother.*, 62(4):746-750, 2008.

Raad et al., "Central venous catheters coated with minocycline and rifampin for the prevention of catheter-related colonization and bloodstream infections. A randomized, double-blind trial," *Ann Intern Med.*, 127(4):267-274, 1997.

Raad et al., "The broad-spectrum activity and efficacy of catheters coated with minocycline and rifampin," *J Infect Dis.*, 173(2):418-424, 1996.

Saint et al., "The clinical and economic consequences of nosocomial central venous catheter-related infection: are antimicrobial catheters useful?" *Infect Control Hosp Epidemiol*, 21(6):375-380, 2000.

Shorr et al., "New choices for central venous catheters: potential financial implications," *Chest*, 124(1):275-284, 2003.

\* cited by examiner

METHOD FOR IMPARTING ANTIMICROBIAL ACTIVITY TO A MEDICAL DEVICE

The present application is a national phase application under 35 U.S.C. §371 of International Application No. PCT/US2010/027768 filed Mar. 18, 2010 which claims the priority benefit of U.S. provisional application No. 61/161,876, filed Mar. 20, 2009 the entire contents of which are incorporated herein by reference.

BACKGROUND

1. Technical Field

The present invention relates generally to a method for imparting antimicrobial activity to a medical device. More particularly, the invention relates to a method for imparting broad spectrum antimicrobial activity by sequentially contacting a medical device with a first antimicrobial component, such as an antiseptic, and a second antimicrobial component, such as a mixture of antibiotics.

2. Background Information

Indwelling medical devices, such as central venous catheters (CVCs), have now become essential tools for use by the medical professional when addressing present-day medical disorders. The benefits derived from these catheters, as well as other indwelling medical devices such as peritoneal catheters, cardiovascular devices, orthopedic implants, penile implants, and other prosthetic devices, have enabled the medical professional to address disorders that had not previously been possible to address by conventional means, or that could only be addressed in a limited manner.

Recent estimates suggest that more than 5 million CVCs are now inserted into patients each year in the United States, with an estimate of 15 million CVC days in intensive care units (ICUs) (the total number of days of exposure to CVCs by all patients in the selected population during the selected time period). However, the use of CVCs is sometimes complicated by catheter-related bloodstream infections (CRBSIs). Colonization of microbials on the surface or other parts of the catheter can produce serious patient problems, including the need to remove and/or replace the CVC, and to vigorously treat any resulting infective conditions.

Reports have shown that between 250,000 and 400,000 vascular catheter-related bacteremias and fungemias occur annually in the United States. Such infections can be life-threatening, and are generally difficult to treat. Approximately 80,000 CRBSIs occur in ICUs, with an average of 5.3 CRBSIs per 1,000 catheter days in the ICU. It is estimated that the mortality rate attributable to CVC infections ranges from about 12 to 25% in critically ill patients, with an increased in-hospital stay ranging from 10 to 20 days, and an added cost ranging from about $4,000 to $56,000 per episode. Almost 70% of CRBSIs are caused by gram-positive organisms, particularly staphylococci such as coagulase negative staphylococci and *Staphylococcus aureus*.

A considerable amount of attention and study has been directed toward preventing microbial colonization. On some occasions, an antimicrobial agent, such as an antibiotic, is coated on the surface of the catheter in an attempt to produce a sufficient bacteriostatic or bactericidal action to reduce or prevent colonization. One early method for preventing bacterial colonization involved coating the catheter with vancomycin. Vancomycin was considered an antibiotic of choice for treating systemic staphylococcal infections, particularly methicillin resistant *S. epidermidis* and *S. aureus*. However, although vancomycin exhibits activity against nonadherent staphylococci in vitro and in human tissue, it is not generally active against staphylococci of the type that adhere to foreign bodies and embed themselves in a layer of biofilm. It is believed that biofilm (slime or fibrous glycocalix) acts as a shield to protect the adherent staphylococci from vancomycin, and to inhibit the activity of glycopeptide antibiotics (vancomycin and teicoplanin). In addition, prophylactic use of vancomycin on a highly colonized surface (such as a catheter) was disfavored for fear that it would promote the emergence of vancomycin resistant staphylococci. Additionally, vancomycin had no activity on fungi, such as *Candida albicans*.

Other investigations into catheter-associated infections showed that bacterial-produced adherent biofilms promote staphylococcal and *Pseudomonas* tolerance to antibiotics normally effective against the same bacteria systemically or in tissue. Evidence of this problem was demonstrated by the inability of tobramycin to kill *Pseudomonas aeruginosa* cells embedded in a biofilm at antibiotic levels of greater than 50 times the minimum bactericidal concentration (MBC) for the identical strain grown in liquid suspension. Nickel et at, *Antimicrob. Agents Chemother.* 27:619-624 (1985). All publications and patent documents referred to throughout this document are incorporated by reference in their entirety. Similarly, six weeks of intensive antibacterial chemotherapy with a β-lactam antibiotic, to which laboratory cultures were exquisitely sensitive, failed to prevent frequent recurrences of a *S. aureus* bacteremia originating from an endocardial pacemaker. Direct examination of the tip of the pacemaker lead revealed that the staphylococci grew in thick slimed enclosed biofilm, which protected the bacteria from very high tissue levels of antibiotic. Subsequent in vitro studies showed the biofilm adherent bacteria were resistant to levels of antibiotics 50 to 100 times higher than the MBC needed to kill non-biofilm encased cells of the same strain. Khoury, A. E. and Costeron J. W., "Bacterial Biofilms in Nature and Disease", *Dialogues in Pediatric Urology*, Vol. 14:2-5 (1991).

Another known method for coating implantable devices with antibiotics involves first coating the selected surfaces with benzalkonium chloride, followed by ionic bonding of the antibiotic composition. See, e.g., Solomon, D. D. and Sherertz, R. J., *J. Controlled Release,* 6:343-352 (1987), and U.S. Pat. No. 4,442,133. Other methods have involved coating a catheter with the antiseptic composition chlorhexidine (CHX), either alone, or in combination with silver sulfadiazine (CHSS). Still other known methods have involved the initial application or absorption on the surface of the medical device of a layer of tridodecylmethyl ammonium chloride (TDMAC) surfactant, followed by an antibiotic coating layer.

Numerous patents describe other methods of coating medical devices with antibiotics. These patents include U.S. Pat. No. 4,895,566 (a medical device substrate carrying a negatively charged group having a pKa of less than 6 and a cationic antibiotic bound to the negatively charged group); U.S. Pat. No. 4,917,686 (antibiotics are dissolved in a swelling agent which is absorbed into the matrix of the surface material of the medical device); U.S. Pat. No. 4,107,121 (constructing the medical device with ionogenic hydrogels, which thereafter absorb or ionically bind antibiotics); U.S. Pat. No. 5,013,306 (laminating an antibiotic to a polymeric surface layer of a medical device); and U.S. Pat. No. 4,952,419 (applying a film of silicone oil to the surface of an implant and then contacting the silicone film bearing surface with antibiotic powders).

Although the methods described in the above-cited references have demonstrated various levels of success in minimizing the extent of bacterial infection, the spectrum of protection available has often been less than desired, and the period of time with which the protection continues has also often been less than desired.

U.S. Pat. No. 5,217,493 teaches an implantable medical device wherein the surface of the device was coated with an antimicrobial composition comprising a combination of antibiotics, such as the antibiotics minocycline and rifampin (M/R). According to the '493 patent, this antimicrobial combination was found to be very effective in killing biofilm-associated staphylococci, particularly *Staphylococcus epidermidis* and *Staphylococcus aureus*, when applied to the surface of an indwelling medical device. The antimicrobial composition was found to be particularly effective with regard to its activity against methicillin-sensitive and resistant staphylococci, and to exhibit broad spectrum inhibitory activity against other gram-positive organisms, such as *enterococci*, *Corynebacterium* and *Bacillus* species. It has been estimated that this antimicrobial composition exhibited favorable activity against resistant staphylococci of the type that account for about 60-70% of CRBSIs.

Although indwelling devices coated with antimicrobial compositions, such as the antimicrobial combinations described in the '493 patent, have generally exhibited effective protection against specified bacteria upon initial implantation, the effectiveness of the protection was subject to diminution over time. During use of the device, the antimicrobial composition may leach from the surface of the device into the surrounding tissue. Over a period of time, the amount of antimicrobials remaining in the device may diminish to an extent that the device no longer provides an optimal level of protection.

U.S. Pat. No. 5,624,704 teaches a medical implant that is impregnated with an antimicrobial, or an antimicrobial combination, such as the minocycline and rifampin (M/R) combination disclosed in the '493 patent. Impregnating the medical implant with these antimicrobials, rather than coating the implant as described in the '493 patent, provided protection for a period of time that in many instances exceeded the duration of protection provided by the coated catheters.

The antimicrobial coated and impregnated catheters disclosed in the '493 and '704 patents demonstrated marked improvement in antimicrobial activity when compared to other commercially available catheters. In vitro and animal studies have shown that M/R coated and impregnated catheters exhibited superior and more prolonged activity against staphylococci when compared with the CHSS-coated catheters described above. In serum at 37° C., the half-life of the antimicrobial activity against *S. epidermidis* of CHSS-coated catheters was 3 days versus 25 days for the M/R-impregnated catheters, with a zone of inhibition ≧15 mm after 30 days of incubation. For other gram-positive organisms that are commonly associated with CRBSIs (e.g., *S. epidermidis*, *S. aureus, Corynebactertiumi*), the mean zone of inhibition was 31.

Another study demonstrated the benefits of M/R-impregnated catheters against catheter-related microbial pathogens when compared to existing antimicrobial catheters. According to this study, after 28 days of being soaked in serum, CVCs impregnated with CHSS, and CVCs impregnated with silver, platinum, and carbon had lost antimicrobial activity against methicillin-resistant *S. aureus* (MRSA) within 14 days. To the contrary, CVCs impregnated with M/R maintained their activity against MRSA for at least 28 days. Hanna H, et al., "Comparative in vitro efficacies and antimicrobial durabilities of novel antimicrobial central venous catheters." *Antimicrob. Agents Chemother.,* 50(10): 3283-8 (2006).

Still another study showed that M/R-coated catheters exhibited significant protection and reduction of staphylococcal adherence, as well as more prolonged antimicrobial durability, against vancomycin-resistant *S. aureus* (VRSA), *Stenotrophomonas maltophilia* and *Acinetobacter* spp. when compared to CHSS and silver, platinum and carbon (SPC) coated catheters, as well as against uncoated catheters. M/R-coated CVCs and CHSS-coated CVCs showed comparable anti-adherence and antimicrobial durability against multi-drug resistant *Enierobacter agglomerans*, but were superior to the SPC and the uncoated catheters. (Hachem R, Chemaly R F, Jiang Y, Reitzel R, Dvorak T, Raad I. Anti-adherence activity and antimicrobial durability of anti-infective-coated catheters against multidrug-resistant (MDR) bacteria. IN: Proceedings of the 47th Interscience Conference on Antimicrobial Agents and Chemotherapy. Chicago, Ill. (Sep. 17-20, 2007)).

Although the antimicrobial-coated and impregnated catheters of the '493 and '704 patents demonstrated marked improvement over other commercially-available catheters, some challenges have persisted. For example, even though the minocycline and rifampin combination demonstrated antimicrobial activity against resistant staphylococci, as well as some resistant gram negative bacteria, the M/R antimicrobial combination did not exhibit significant activity against *Pseudomonas aeruginosa*, and against fungi such as *Candida parapsilosis, Candida albicans* and the more resistant *Candida krusei*. (Hanna H, et al, supra.) *Pseudomonas aeruginosa* is considered the most virulent gram negative bacteria causing catheter-related bacteremia. *Candida parapsilosis, Candida albicans* and *Candida krusei* have been implicated in causing catheter-related *Candidemia*, which is associated with very high rates of morbidity and mortality.

A need persists for a method for providing efficacious broad spectrum anti-infective protection to a medical device, including but not limited to, protection against resistant staphylococci, MDR gram negative bacteria (such as MDR *Pseudomonas aeruginosa*), and resistant *Candida* (e.g., *C. krusei*).

DETAILED DESCRIPTION

Figure 1:
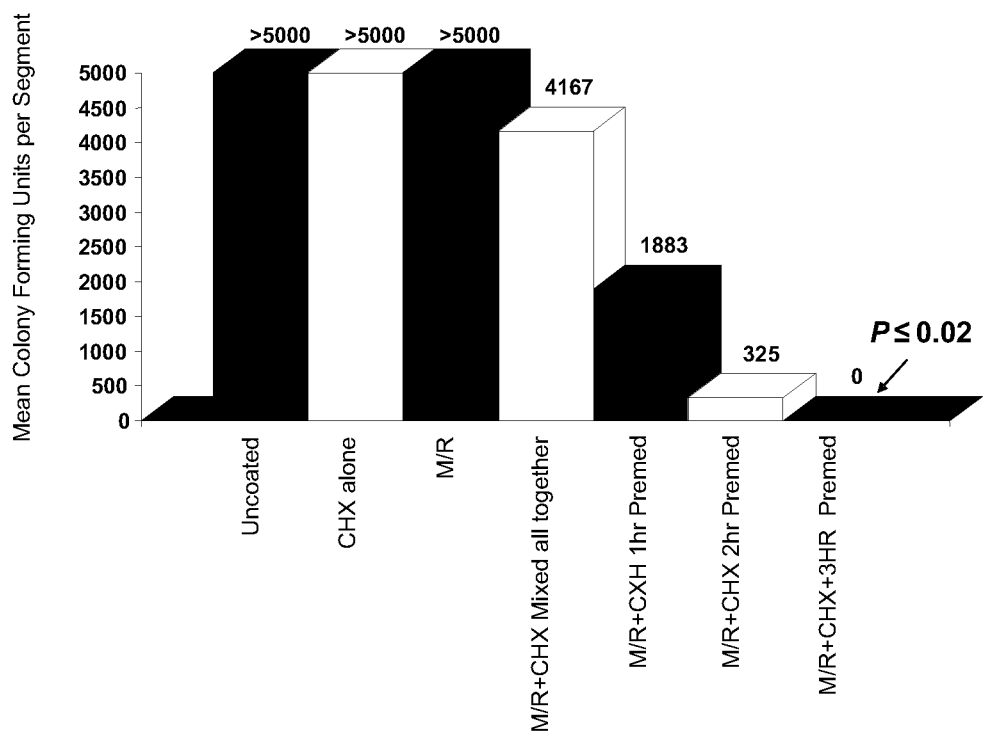
FIG. 1 illustrates the adherence of *C. albicans* to various polyurethane catheters coated/impregnated with chlorhexidine and/or minocycline/rifampin.

In accordance with the present invention, there is provided a method for imparting broad spectrum antimicrobial activity to a medical device. The medical device is sequentially contacted with a solution containing a first antimicrobial component, such as an antiseptic (for example, a guanidium compound), and a solution containing a second antimicrobial component, such as a combination of antibiotics (for example, a combination of a tetracycline and a rifamycin).

The invention also relates to a medical device formed according to the inventive method. The medical device is capable of providing broad spectrum antimicrobial activity in preventing the adherence of, e.g., resistant *S. aureus*, as well as resistant *Pseudomonas aeruginosa*, and *Candida krusei* and *C. albicans*, when compared to medical devices coated/impregnated with an antiseptic (e.g., chlorhexidine) alone, a mixture of antibiotics (e.g., minocycline and rifampin) alone, or even a simultaneous mixture of the antiseptic and antibiotics.

The terms "antimicrobial medical device" and "medical device" as used herein, refer to an instrument, apparatus, implement, machine, contrivance, implant, or other similar or related article, including a component part, or accessory, which is subjected to sequential antimicrobial contact as described, and is intended for use in the diagnosis, treatment, and/or prevention of disease or other health-related condition in a subject. The subject can be any vertebrate, such as a mammal. Non-limiting examples of antimicrobial medical devices include vascular catheters, such as peripherally insertable central venous catheters, dialysis catheters, long term tunneled central venous catheters, peripheral venous catheters, single-lumen and multiple-lumen short-term central venous catheters, arterial catheters, pulmonary artery Swan-Ganz catheters, and the like; urinary catheters, other long term urinary devices, tissue bonding urinary devices, renal stents, penile prostheses, vascular grafts, vascular access ports, wound drain tubes, hydrocephalus shunts, ventricular drainage catheters, neurologic and epidural catheters, neurostimulators, peritoneal dialysis catheters, pacemaker capsules, artificial urinary sphincters, small or temporary joint replacements, dilators, heart valves, orthopedic prosthesis, spinal hardware, surgical site repair mesh (e.g., hernia mesh), endotracheal tubes, biliary stents, gastrointestinal tubes, gloves (including latex, non-latex and nitrile), other medical garb, charts, bed rails, condoms, colorectal tract implants, male and female reproductive implants, cosmetic or reconstructive implants (e.g., breast, chin, cheek, buttock, nasal), medical device envelopes and pouches, including stethoscope drums, orthopedic implants (e.g., joint (knee, hip, elbow, shoulder, ankle), prostheses, external fixation pins, intramedullary rods and nails, spine implants), other medical and indwelling devices that may be subject to microbial infestation and/or activity; and metallic devices, such as cardiac pacemakers, defibrillators, electronic device leads, adaptors, lead extensions, implantable infusion devices, implantable pulse generators, implantable physiological monitoring devices, devices for locating an implantable pulse generator or implantable infusion device under the skin, and devices (e.g. refill needles and port access cannulae) for refilling an implantable infusion device.

The term "antimicrobial agent", as used herein, refers to an agent, such as an antibiotic or an antiseptic, that is capable of preventing or reducing the growth or reproduction of a microorganism, such as a bacterial or fungal microorganism, or of killing a microorganism.

The term "antibiotic" as used herein refers to a compound or agent that is capable of preventing or reducing the growth or reproduction of a bacterium, or of killing a bacterium. Such agents are generally applied in the treatment of systemic infection in a subject. Non-limiting classes of antibiotics referred to herein include any tetracycline known to those of ordinary skill in the art, such as minocycline, and any rifamycin known to those of ordinary skill in the art, such as rifampin.

The term "antiseptic" as used herein refers to a compound or agent that is capable of preventing or reducing the growth or reproduction of a microorganism (such as bacteria, fungi, protozoa, and viruses), or of killing a microorganism, but which is generally not applied in the treatment of a systemic infection in a subject, usually because of limitations related to absorption, penetration, or systemic toxicity. A non-limiting class of antiseptics that can be used includes guanidium compounds, such as chlorhexidine.

Minocycline is a semisynthetic antibiotic derived from tetracycline. It is primarily bacteriostatic and exerts its antimicrobial effect by inhibiting protein synthesis. Minocycline is commercially available as the hydrochloride salt which occurs as a yellow, crystalline powder and is soluble in water and slightly soluble in organic solvents including alcohols, ketones, ethers, aldehydes, acetonitrile, acetic acid, methylene chloride and chloroform. Minocycline is active against a wide range of gram-positive and gram-negative organisms.

Rifampin is a semisynthetic derivative of rifamycin B, a macrocyclic antibiotic compound produced by the mold *Streptomyces mediterranic*. Rifampin inhibits bacterial DNA-dependent RNA polymerase activity and is bactericidal in nature. Rifampin is commercially available as a red-brown crystalline powder and is very slightly soluble in water and freely soluble in acidic aqueous solutions and organic solutions including alcohols, ketones, ethers, aldehydes, acetonitrile, acetic acid, methylene chloride and chloroform. Rifampin possesses a broad spectrum activity against a wide range of gram-positive and gram-negative bacteria.

Chlorhexidine is an antiseptic cleansing agent that is active against staphylococci and other gram-positive bacteria, as well as against various fungi. Chlorhexidine is soluble in both water and organic solutions including alcohols, ketones, ethers, aldehydes, acetonitrile, acetic acid, methylene chloride and chloroform. When utilized herein, the term chlorhexidine may include salts of chlorhexidine.

The term "organic solvent" as used herein refers to a solvent that can be used to dissolve antimicrobial agents, and includes, among others, alcohols (e.g., methanol, ethanol), ketones (e.g., acetone, methylethylketone), ethers (e.g., tetrahydrofuran), aldehydes (e.g., formaldehyde), acetonitrile, acetic acid, methylene chloride and chloroform.

The term "penetrating agent" as used herein refers to an agent, such as an organic compound, that is capable of promoting penetration of an antimicrobial agent, such as a guanidium compound, into the matrix of the medical device. Non-limiting examples of such compounds are esters (e.g., ethyl acetate, propyl acetate, butyl acetate, amyl acetate, and combinations thereof), ketones (e.g., acetone and methylethylketone), methylene chloride and chloroform.

The term "alkalinizing agent" as used herein refers to organic and inorganic bases, including sodium hydroxide, potassium hydroxide, ammonia in water (e.g., 27% ammonium hydroxide), diethylamine and triethylamine.

The term "bacterial and fungal organisms" as used in the present invention means all genuses and species of bacteria and fungi, including but not limited to all spherical, rod-shaped, and spiral bacteria. Non-limiting examples of bacteria include staphylococci (e.g., *Staphylococcus epidermidis, Staphylococcus aureus*), *Enterrococcus faecalis, Pseudomonas aeruginosa, Escherichia coli*, among other gram-positive bacteria and gram-negative bacilli. Non-limiting examples of fungal organisms include *Candida albicans* and *Candida krusei*.

Medical devices that are amenable to treatment according to the method of the present invention generally include non-metallic materials, such as rubber, plastic, polyethylene, polyurethane, silicone, polytetrafluoroethylene (PTFE), polyethylene terephthalate (PET), latex, nitrile, and other polymeric and elastomeric materials, as well as metals, such as titanium, and metal alloys, such as stainless steel and nitinol. Those skilled in the art will appreciate that the listing of non-metals, metals, and metal alloys as described herein is exemplary only, and is not intended to be exclusive. Other materials that are amenable to treatment as described herein are also within the scope of the present invention.

A feature of the present invention involves the sequential treatment, or contact, of the medical device with a first antimicrobial component, and thereafter with a second antimicrobial component. In a preferred embodiment, the first antimicrobial component comprises an antiseptic, such as a guanidium compound (e.g., chlorhexidine, alexidine, and hexamidine). In the preferred embodiment, the second antimicrobial component comprises a mixture of antibiotics, such as a mixture of a tetracycline and a rifamycin. Preferably, the second antimicrobial component comprises a mixture of minocycline and rifampin.

In at least some embodiments set forth herein, one or more of the contacting steps are carried out by heating the composition. As used herein, "heating" refers to an increase in the temperature of a composition due to application of a heat source, when compared to the temperature of the composition in the absence of the heat source. Heating can be by any method known to those of ordinary skill in the art. The presence of heat in the contacting step is believed to enhance the adherence of the antimicrobial agent to the medical device.

In at least some embodiments set forth herein, the medical device is washed following the sequential contact with the antimicrobial components. As used herein, "washing" refers to the application of a liquid to the medical device for the purpose of removing a substance. For example, washing may be further defined as contacting the surface of the medical device with de-ionized water. The contacting may result in removal of antimicrobial agent and solvent not bound to the medical device. Any method known to those of ordinary skill in the art can be applied in washing the medical device. Washing can, for example, include rinsing, dipping, or immersing the device in a wash solution using any method known to those of ordinary skill in the art.

Additional details regarding contacting an antimicrobial with a medical device not specifically recited herein can be found, e.g., in U.S. Pat. Nos. 5,217,493, 5,624,704, 5,902,283, and 7,651,661, as well as in U.S. Patent App. Pub. Nos. 2005/0197634, 2003/0078242, and 2007/0154621, all incorporated by reference.

When the antimicrobial medical device is non-metallic (i.e., it is not a metal or a metal alloy), it is preferred, but not required, to impregnate the first antimicrobial component into the matrix of the non-metallic device. While coating the surface of the non-metallic medical device with the first antimicrobial component does provide protection against microbials initially, over a period of time the antimicrobial component may leach from the surface of the medical device into the surrounding environment, thereby diminishing the effectiveness of the coating. Impregnation of the first antimicrobial component, e.g., chlorhexidine, into the matrix of the non-metallic device typically enables the device to retain the antimicrobial ability provided by this component for a longer period of time, when compared to devices that are coated with the same antimicrobial. A penetrating agent and/or an alkalinizing agent may be added to the solution of the first antimicrobial component to facilitate penetration of the antimicrobial into the matrix of the device. It is not typically necessary to determine whether a particular application of the first antimicrobial compound has penetrated the substrate to a particular depth. Therefore, on occasion, the treatment with the first antimicrobial compound may be referred to as either a coating or an impregnation. Following coating or impregnation of the first antimicrobial component, the device is then coated with the second antimicrobial component.

When the antimicrobial medical device is a metal or a metal alloy, the first antimicrobial component is typically coated on the medical device. This step is then followed by coating the device with the second antimicrobial component in the same manner as with a non-metallic device. Although a certain amount of infusion or impregnation into the matrix of the metal or metal alloy may occur as a result of the coating with the first antimicrobial component, it is not generally necessary to take any specific actions to achieve infusion or impregnation.

In a preferred embodiment, the first antimicrobial component may be prepared by dissolving chlorhexidine (CHX), or a salt of chlorhexidine (e.g., chlorhexidine diacetate (CHD)), in a suitable organic solvent. At least a portion of the medical device is inserted into this solution under conditions sufficient to impregnate the CHX into the matrix of the medical device portion. The second antimicrobial component may be prepared by initially dissolving an alkalinizing agent in an organic solvent, and then sequentially dissolving minocycline and rifampin (M/R) in the organic solvent/alkalinizing agent. The second solution may be added to the first solution comprising the medical device under conditions suitable for coating the CHX-impregnated device with M/R. Alternatively, instead of combining the two solutions as described, the medical device may be removed from the first solution following impregnation, and then inserted into the second solution for coating.

Each of the first and second solutions is preferably heated to a temperature between about 30° C. and 70° C., and more preferably, about 45° C. prior to mixing the respective solutions. Heating the first solution improves the saturation of CHX into the matrix of the medical device. Heating the second solution improves the adherence of the M/R antimicrobials to the medical device.

The following examples involve application of the first and second antimicrobial components to a non-metallic substrate. Those skilled in the art will appreciate that application of the antimicrobial components to a metal or metal alloy substrate may also be carried out by a similar procedure, with minor modification as indicated above. The examples are provided by way of illustration only, and are not intended to limit the scope of the invention in any manner.

Example 1

In this example, comparative tests were carried out to compare the antimicrobial activity on central venous catheter (CVC) segments. Three Positive Control Samples were prepared according to known methods. Five Inventive Samples were prepared according to a method of the present invention.

Those skilled in the art will appreciate that the respective concentrations of the solutions of the first antimicrobial component, in this case chlorhexidine, and the second antimicrobial component, in this case minocycline/rifampin, as described in the following examples are exemplary only, and that other concentrations, as well as other ratios of CHX to M/R, may be substituted. When the teachings of this method are utilized, only minimal experimentation will be required to arrive at concentrations and application conditions appropriate for use in imparting antimicrobial activity to a particular medical device that is intended to be utilized for a particular purpose.

POSITIVE CONTROL SAMPLE 1. Polyurethane central venous catheters (CVCs) were impregnated with minocycline/rifampin (M/R) according to the following procedure:

Formula:
NaOH—10 mg/mL dissolved in Methanol
Minocycline—15 mg/mL
Rifampin—30 mg/mL
Methanol—15%
Butyl Acetate—85%
Procedure:
**Note—all calculations are based on a 50 mL final volume of solution.
Add 1 pellet of NaOH (~10 mg/mL) to 7.5 mL of Methanol, stir at 45° C. until dissolved. Once dissolved add 0.75 g of Minocycline to the NaOH/MetOH solution in small aliquots over 1 hour while continuously stirring at 45° C. Add 1.5 g of Rifampin to the solution in small aliquots over 15 minutes while continuously stirring at 45° C.
Impregnate catheter segments by placing the catheters in the solution for 1 hour while continuously stirring at 45° C.
After impregnating, remove catheters from solution and air flush to remove any excess coating solution from the lumens. Dry the impregnated catheters overnight at 60° C. Next day, wash the catheters vigorously 3 times with de-ionized water. Remove excess water by rubbing catheter segments with paper towels. Catheters are then dried for an additional 4 hrs at 60°

POSITIVE CONTROL SAMPLE 2. Polyurethane CVCs were impregnated with chlorhexidine according to the following procedure:
Formula:
20 mg/mL Chlorhexidine (CHX)
100% Butyl Acetate (BA)
Procedure:
**Note—all calculations are based on a 50 mL final volume of solution.
Add 1 g of CHX to 50 mL Butyl Acetate. Stir for 1 hour at room temperature to dissolve CHX. Impregnate the catheter segments in the CHX+BA solution with stirring at room temperature for 1 hour
After impregnating the catheters segments, remove the catheters from solution and air flush to remove any excess coating solution from the lumens. Dry the CHX-impregnated catheters overnight at 60° C. Next day, wash the catheters vigorously 3 times with de-ionized water. Remove excess water by rubbing catheter segments with paper towels. Catheters are then dried for an additional 4 hrs at 60°

POSITIVE CONTROL SAMPLE 3. Polyurethane CVCs were simultaneously coated with a minocycline/rifampin+chlorhexidine solution according to the following procedure:
Formula:
10 mg/mL NaOH
20 mg/mL Chlorhexidine (CHX)
15 mg/mL Minocycline
30 mg/mL Rifampin
15% Methanol (MetOH)
85% Butyl Acetate (BA)
Procedure:
**Note—all calculations are based on a 50 mL final volume of solution.
Add 1 g of CHX to 42.5 mL Butyl Acetate. Stir for 1 hour at room temperature to dissolve CHX. Simultaneously prepare M/R solution as follows.
Add 1 pellet of NaOH (~10 mg/mL) to 7.5 mL of Methanol, stir at 45° C. until dissolved. Once dissolved add 0.75 g of Minocycline to the NaOH/MetOH solution in small aliquots over 1 hour while continuously stirring at 45° C. Add 1.5 g of Rifampin to the solution in small aliquots over 15 minutes while continuously stirring at 45° C.
Add the M/R in MetOH solution to the CHX in BA solution. Coat catheter segments for 1 Hour while continuously stirring at 45° C.
After coating, remove catheters from solution and air flush to remove any excess coating solution from the lumens. Dry the coated catheters overnight at 60° C. Next day, wash the catheters vigorously 3 times with de-ionized water. Remove excess water by rubbing catheter segments with paper towels. Catheters are then dried for an additional 4 hrs at 60°

INVENTIVE SAMPLE 1. Polyurethane CVCs were treated according to a method of the present invention with 1 hr CHX pre-medication as follows:
Formula:
10 mg/mL NaOH
20 mg/mL Chlorhexidine (CHX)
15 mg/mL Minocycline
30 mg/mL Rifampin
15% Methanol (MetOH)
85% Butyl Acetate (BA)
Procedure:
**Note—all calculations are based on a 50 mL final volume of solution.
Add 1 g of CHX to 42.5 mL Butyl Acetate. Stir for 1 hour at 45° C. to dissolve CHX. Coat the catheter segments in the CHX+BA solution stirring at 45° C. for 1 hour. Simultaneously prepare the M/R solution as follows.
Add 1 pellet of NaOH (~10 mg/mL) to 7.5 mL of Methanol, stir at 45° C. until dissolved. Once dissolved add 0.75 g of Minocycline to the NaOH/MetOH solution in small aliquots over 1 hour while continuously stirring at 45° C. Add 1.5 g of Rifampin to the solution in small aliquots over 15 minutes while continuously stirring at 45° C.
After the 1 hr coat in CHX, add the M/R MetOH solution to the catheters segments in CHX+BA solution. Coat the catheter segments for 1 hour while continuously stirring at 45° C.
After coating, remove the catheters from solution and air flush to remove any excess coating solution from the lumens. Dry the coated catheters overnight at 45° C. Next day, wash the catheters vigorously 3 times with de-ionized water. Remove excess water by rubbing catheter segments with paper towels. Catheters are then dried for an additional 4 hrs at 45°

INVENTIVE SAMPLE 2. Polyurethane CVCs were coated according to a method of the present invention with 2 hr CHX pre-medication as follows:
Formula:
10 mg/mL NaOH
20 mg/mL Chlorhexidine (CHX)
15 mg/mL Minocycline
30 mg/mL Rifampin
15% Methanol (MetOH)
85% Butyl Acetate (BA)

Procedure:

**Note—all calculations are based on a 50 mL final volume of solution.

Add 1 g of CHX to 42.5 mL Butyl Acetate. Stir for 1 hour at 45° C. to dissolve CHX. Coat the catheter segments in the CHX+BA solution by stirring at 45° C. for 2 hours. After 1 hr begin preparing M/R solution as follows.

Add 1 pellet of NaOH (~10 mg/mL) to 7.5 mL of Methanol, stir at 45° C. until dissolved. Once dissolved add 0.75 g of Minocycline to the NaOH/MetOH solution in small aliquots over 1 hour while continuously stirring at 45° C. Add 1.5 g of Rifampin to the solution in small aliquots over 15 minutes while continuously stirring at 45° C.

After the 2 hr coat in CHX add the M/R in MetOH solution to the catheter segments in CHX+BA solution. Incubate the catheters for an additional hour in the M/R+CHX solution while continuously stirring at 45° C.

After the 3 hr total coating time, remove the catheters from the solution and air flush to remove any excess coating solution from the lumens of the catheters. Dry the coated catheters overnight in a 45° C. incubator. Next day, wash vigorously the catheters 3 times with de-ionized water. Remove excess water with paper towels. Catheters are then dried for an additional 4 hrs at 45° C.

INVENTIVE SAMPLE 3. Polyurethane CVCs were coated according to a method of the present invention with 3 hr CHX pre-medication as follows:

Formula:
10 mg/mL NaOH
20 mg/mL Chlorhexidine (CHX)
15 mg/mL Minocycline
30 mg/mL Rifampin
15% Methanol (MetOH)
85% Butyl Acetate (BA)

Procedure:

**Note—all calculations are based on a 50 mL final volume of solution.

Add 1 g of CHX to 42.5 mL Butyl Acetate. Stir for 1 hour at 45° C. to dissolve CHX. Coat the catheter segments in the CHX+BA solution by stirring at 45° C. for 3 hours. After 2 hr begin preparing the M/R solution as follows.

Add 1 pellet of NaOH (~10 mg/mL) to 7.5 mL of Methanol, stir at 45° C. until dissolved. Once dissolved add 0.75 g of Minocycline to the NaOH/MetOH solution in small aliquots over 1 hour while continuously stirring at 45° C. Add 1.5 g of Rifampin to the solution in small aliquots over 15 minutes while continuously stirring at 45° C.

After the 3 hr coat in CHX add the M/R in MetOH solution to the catheter segments in CHX+BA. Incubate the catheters for an additional hour in the M/R+CHX solution while continuously stirring at 45° C.

After the 4 hr total coating time, remove the catheters from solution and air flush to remove any excess coating solution from the lumens of the catheters. Dry the coated catheters overnight in a 45° C. incubator. Next day, wash vigorously the catheters 3 times with de-ionized water. Remove excess water with paper towels. Catheters are then dried for an additional 4 hrs at 45° C.

INVENTIVE SAMPLE 4. Polyurethane CVCs were coated according to a method of the present invention with 4 hr CHX pre-medication as follows:

Formula:
10 mg/mL NaOH
20 mg/mL Chlorhexidine (CHX)
15 mg/mL Minocycline
30 mg/mL Rifampin
15% Methanol (MetOH)
85% Butyl Acetate (BA)

Procedure:

**Note—all calculations are based on a 50 mL final volume of solution.

Add 1 g of CHX to 42.5 mL Butyl Acetate. Stir for 1 hour at 45° C. to dissolve CHX. Coat the catheter segments in the CHX+BA solution by stirring at 45° C. for 4 hours. After 3 hr begin preparing M/R solution as follows.

Add 1 pellet of NaOH (~10 mg/mL) to 7.5 mL of Methanol, stir at 45° C. until dissolved. Once dissolved add 0.75 g of Minocycline to the NaOH/MetOH solution in small aliquots over 1 hour while continuously stirring at 45° C. Add 1.5 g of Rifampin to the solution in small aliquots over 15 minutes while continuously stirring at 45° C.

After the 4 hr CHX coating add the M/R in MetOH solution to the catheter segments in CHX+BA. Incubate the catheters for an additional hour in the M/R+CHX solution while continuously stirring at 45° C.

After the 5 hr total coating time, remove the catheters from the solution and air flush to remove any excess coating solution from the lumens of the catheters. Dry the coated catheters overnight in a 45° C. incubator. Next day, wash vigorously the catheters 3 times with de-ionized water. Remove excess water with paper towels. Catheters are then dried for an additional 4 hrs at 45° C.

INVENTIVE SAMPLE 5. Polyurethane CVCs were coated according to a method of the present invention with 5 hr CHX pre-medication as follows:

Formula:
10 mg/mL NaOH
20 mg/mL Chlorhexidine (CHX)
15 mg/mL Minocycline
30 mg/mL Rifampin
15% Methanol (MetOH)
85% Butyl Acetate (BA)

Procedure:

**Note—all calculations are based on a 50 mL final volume of solution.

Add 1 g of CHX to 42.5 mL Butyl Acetate. Stir for 1 hour at 45° C. to dissolve CHX. Coat the catheter segments in the CHX+BA solution by stirring at 45° C. for 5 hours. After 4 hr begin preparing M/R solution as follows.

Add 1 pellet of NaOH (~10 mg/mL) to 7.5 mL of Methanol, stir at 45° C. until dissolved. Once dissolved add 0.75 g of Minocycline to the NaOH/MetOH solution in small aliquots over 1 hour while continuously stirring at 45° C. Add 1.5 g of Rifampin to the solution in small aliquots over 15 minutes while continuously stirring at 45° C.

After the 5 hr CHX coating add the M/R in MetOH solution to the catheter segments in CHX+BA. Incubate the catheters for an additional hour in the M/R+CHX solution while continuously stirring at 45° C.

After the 6 hr total coating time, remove the catheters from the solution and air flush to remove any excess coating solution from the lumens of the catheters. Dry the coated catheters overnight in a 45° C. incubator. Next day, wash vigorously the catheters 3 times with de-ionized water. Remove excess water with paper towels. Catheters are then dried for an additional 4 hrs at 45° C.

Following treatment of the CVCs in the respective Positive Control Samples 1-3 and Inventive Samples 1-5, tests were carried out to measure the adherence of certain bacterial and fungal organisms on the treated CVCs. Six catheter segments (n=6) were tested from each group. These tests were modified from the biofilm adherence protocol described in the following publications: Kuhn D M, George T, Chandra J, Mukherjee P K, and Ghannoum M A. "Antifungal Susceptibility of Candida Biofilms: Unique Efficacy of Amphotericin B Lipid Formulations and Echinocandins", *Antimicrobial Agents and Chemotherapy*, 46, 1773-80 (2002); Hanna H, Bahna P, Reitzel R, Dvorak T, Chaiban G, Hachem R, Raad I. "Comparative in vitro efficacies and antimicrobial durabilities of novel antimicrobial central venous catheters", *Antimicrobial Agents Chemotherapy*, 50(10), 3283-8 (2006); Chaiban G, Hanna H, Dvorak T, Raad I. "A Rapid Method of Impregnating Endotracheal Tubes and Urinary Catheters with Gendine: A Novel Antiseptic Agent", *J Antimicrob Chemother.*, 55(1): 51-6 (2005); and Raad I, Reitzel R, Jiang Y, Chemaly R F, Dvorak T, Hachem R. "Anti-adherence Activity and Antimicrobial Durability of Anti-infective-coated Catheters against Multidrug Resistant Bacteria", *J Antimicrob Chemother.*, 62(4):746-50 (2008), all of the foregoing incorporated by reference herein.

In the following tests, 7 French CVCs (Cook Medical, Bloomington, Ind.) were cut into 1 cm segments, and treated as described above. The segments were initially placed into respective wells of a 24-well tissue culture plate containing 1 ml donor plasma, and incubated for 24 hrs at 37° C. The following day the plasma was removed and discarded, and replaced with a 1 ml bacterial or fungal (Candida) solution at a final concentration of $5.5 \times 10^5$ cells/ml in Muller Hinton broth. The plates were incubated for 24 hrs at 37° C. The media was then removed and discarded. The media was replaced with 1 ml of a 0.9% sterile saline solution, and the segments were washed with shaking at 37° C. for 30 min. The catheter segments were then carefully removed with sterile wood sticks and placed in separate sterile closed tubes containing 5 ml 0.9% saline solution, wherein they were sonicated for 15 min. After sonication, the tubes were vortexed, and 100 μl of the microbial solution (1:50 dilution) was spread on TSA+5% sheep blood plates for the testing of bacterial samples, or on Sabaroud Dextrose Agar (SAB) plates for the testing of yeasts. The plates were incubated inverted at 37° C. for 24 hrs. Colonies were then counted after 24 hrs. Any raw colony counts over 100 colonies were considered to be >100. Dilution factors (1:50) were taken into account, and final counts were defined as colony forming units per catheter segment.

The results of the tests are graphically provided at FIGS. 1-4. As shown in FIG. 1, the catheters that were pre-treated in the chlorhexidine solution for at least one hour, with subsequent addition of minocycline and rifampin were much more effective than uncoated control catheter samples, as well as with Positive Control Samples coated with CHX alone, M/R alone, and M/R+CHX simultaneously mixed together, respectively, in preventing and protecting against the adherence of *Candida albicans* against catheter surfaces. The inventive samples with at least a 2 hour pre-treatment in CHX were significantly more effective than the control samples ($P \leq 0.02$). *Candida albicans* contributes to the majority of catheter-related candidemias.

Figure 2:
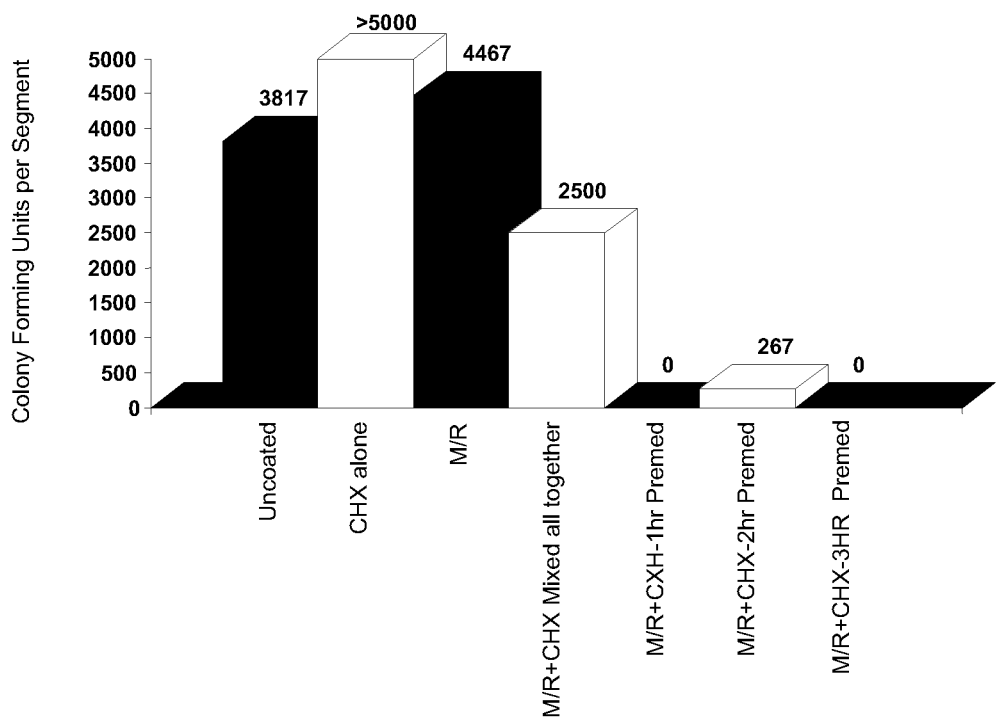
FIG. 2 illustrates the adherence of *C. krusei* to various polyurethane catheters coated/impregnated with chlorhexidine and/or minocycline/rifampin.

As shown in FIG. 2, the catheters that were pre-treated with chlorhexidine for at least one hour with subsequent addition of minocycline and rifampin were significantly more effective than uncoated control samples, as well as the Positive Control Samples coated with CHX alone, and with M/R alone, respectively, in preventing and protecting against the adherence of *Candida krusei* against catheter surfaces ($P \leq 0.01$). Less dramatic, but still significant, results were obtained when compared to Positive Control Samples having M/R and CHX mixed together (Positive Control 3).

Figure 3:
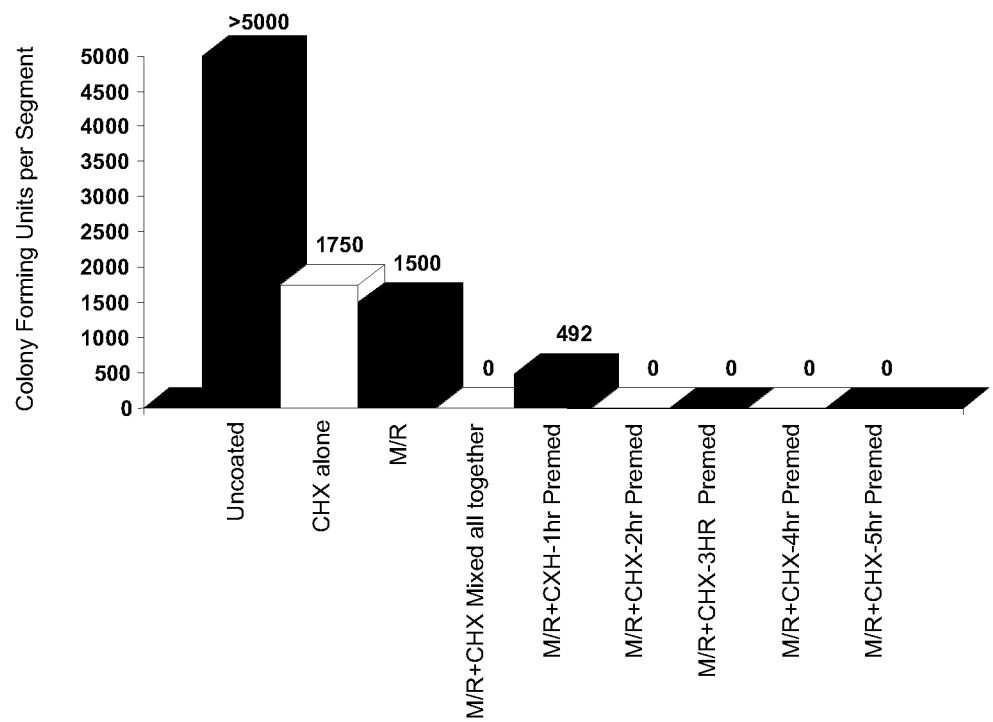
FIG. 3 illustrates the adherence of methicillin-resistant *S. aureus* (MRSA) to various polyurethane catheters coated/impregnated with chlorhexidine and/or minocycline/rifampin.

As shown in FIG. 3, the inventive samples that were pre-saturated with CHX for at least one hour were highly effective in completely preventing and protecting catheters from the adherence of methicillin-resistant *S. aureus* (MRSA) in a manner that is equivalent to or greater than the coated with M/R alone, and significantly superior to catheters coated with CHX alone or uncoated catheters. The inventive samples with at least a 2 hour premedication in CHX were significantly more effective than the control samples ($P \leq 0.01$). There did not appear to be any measurable difference between the catheters that were pre-treated with CHX for two hours, when compared to catheters pre-treated for three, four and five hours, respectively.

Figure 4:
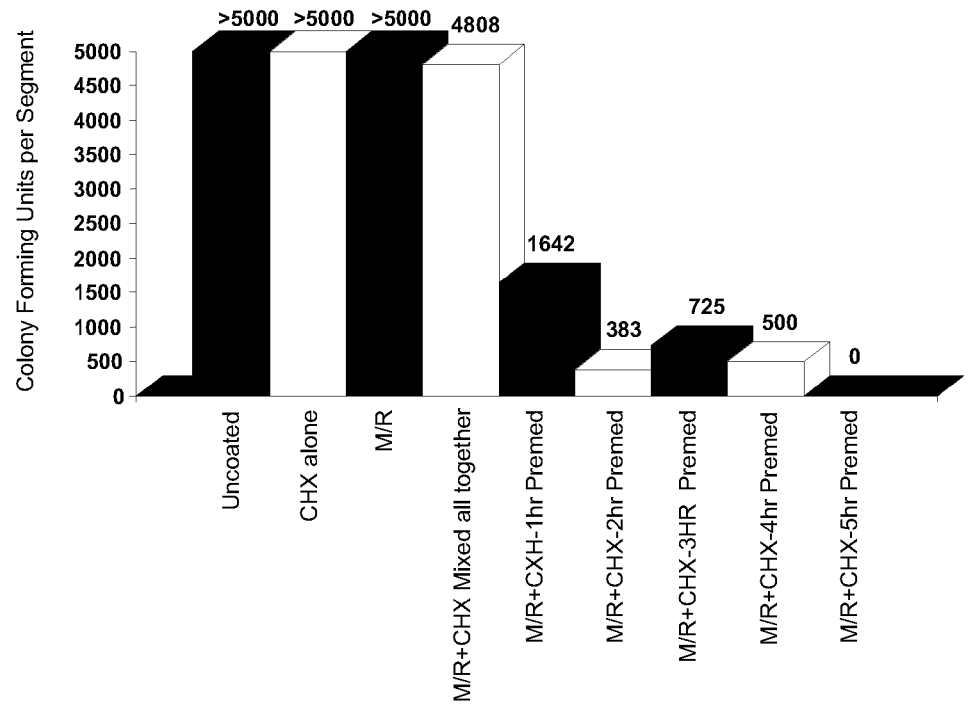
FIG. 4 illustrates the adherence of MDR *Pseudomonas aeruginosa* to various polyurethane catheters coated/impregnated with chlorhexidine and/or minocycline/rifampin.

Similarly, FIG. 4 above shows that the inventive samples that were pre-treated with CHX for a period of at least one hour were very effective in preventing and protecting the adherence of resistant *P. aeruginosa*, in a manner that is superior to uncoated catheters, catheters coated with CHX alone, M/R alone, or even M/R+CHX simultaneously mixed together. When the CHX pre-treatment is carried out for at least two hours, the catheters were found to be highly effective in preventing and protecting the adherence of resistant *P. aeruginosa* ($P \leq 0.01$). According to FIG. 4, if the pre-treatment period is extended beyond 4 hours, almost complete prevention is observed at 5 hours.

As demonstrated above, by pre-treating the medical device with the antiseptic compound (in this case, CHX) under heat, and subsequently exposing the device to the antibiotic (in this case, M/R) component as described, a broad spectrum of antimicrobial protection is provided to the medical device. This broad spectrum protection is capable of preventing the adherence of resistant bacteria and fungi, such as *Pseudomonas aeruginosa, S. aureus, Candida krusei* and *albicans*, in a manner superior to the catheters coated with M/R alone, CHX alone, or even M/R+CHX simultaneously mixed together. Furthermore, this novel pre-treated catheter maintained excellent antimicrobial activity against (the adherence of) staphylococci, and represented an improvement over catheters treated with minocycline/rifampin or chlorhexidine alone.

CHX alone has little activity on its own against *P. aeruginosa* and *Candida* species. Furthermore, if CHX is simply mixed simultaneously with minocycline and rifampin, and the catheter is treated with the combined (CHX+M/R) solution, comparatively little activity would be demonstrated against *C. albicans, C. parapsilosis, S. aureus*, or *P. aeruginosa*. M/R coated catheters have no activity against the most virulent organisms that can cause catheter-related bloodstream infections (CRBSI), namely *P. aeruginosa* and *Candida*. Impregnating or otherwise coating catheters with CHX through this pre-treatment method, followed by the coating of the catheters with minocycline/rifampin, results in an antimicrobial catheter that has broad spectrum activity against microbial pathogens that can cause CRBSI, including staphylococci, and gram-negative bacteria, such a *P. aeruginosa* and fungi (such as *Candida*).

Example 2

In this example, comparative tests were carried out on silicone breast implant segments. In use, the coating solution can be applied to implants in the operating room immediately prior to surgery to reduce the risk of microbial biofilm formation. As stated, medical devices impregnated with antimicrobials have been shown to significantly reduce and prevent incidence of infection. Breast augmentation or reconstruction with implants has been associated with colonization of *Staphylococcus epidermidis* often resulting in capsular contracture.

Coating Procedure: In the comparative tests as described below, segments of silicone breast implant shells were coated in the following manner:

POSITIVE CONTROL SAMPLE:
300 mg of Minocycline and 600 mg of Rifampin were dissolved in 20 mL of MetOH. Segments were coated for 60 min in the M/R solution. Segments were then dried in ambient conditions for 10 minutes.
The concentrations of drug in the test solution was 15 mg/mL Minocycline, and 30 mg/mL Rifampin INVENTIVE SAMPLE:
400 mg Chlorhexidine diacetate (CHD) was dissolved in 10 mL of Methanol (MetOH). Segments were coated for 30 min in the CHD solution. Simultaneously, 300 mg of Minocycline and 600 mg of Rifampin were dissolved in a separate 10 mL of MetOH. After the initial 30 min coating, the M/R solution was added to the CHD solution and segments were coated for an additional 30 minutes. Segments were then dried in ambient conditions for 10 minutes.
The concentrations of drug in the presaturation and final solutions were as follows:
  A. Presaturation—40 mg/mL CHD in MetOH
  B. Final Solution—20 mg/mL CHD, 15 mg/mL Minocycline, and 30 mg/mL Rifampin Antimicrobial efficacy was determined according to a Modified Kuhn's method protocol. Coated catheter segments, tested in triplicate, were incubated for 24 hours with $5.0 \times 10^5$ cells in Muller Hinton Broth of various organisms and incubated for an additional 24 hours. After incubation, the bacterial innoculum was discarded and segments were washed shaking for 30 minutes in 1 mL of 0.9% sterile saline. The segments were then removed with sterile sticks placed in 5 mL of 0.9% sterile saline and sonicated for 15 minutes. After sonication, each sample was vortexed for 5 seconds, and 100 µL of liquid from each segment was serially diluted and spread onto Trypticase Soy Agar+5% Sheep Blood (for bacteria) or Sabouraud Dextrose Agar (for yeast) for quantitative culture. Plates were then incubated at 37 C.° inverted for 24 hours and counted for colony growth. The specific organisms tested comprised Methicillin Resistant *Staphylococcus epidermidis* (MRSE Frietas).

The results of this test are provided in Table 1 below, and in FIG. 5.

TABLE 1

| MRSE (Staph epi) | BASELINE | 2 DAY |
|---|---|---|
| Control | $5.50 \times 10^6$ | $5.50 \times 10^6$ |
| 1 hr M/R | 516.7 | 1016.7 |
| 30 min CHD + 30 min M/R | 0 | 0 |

Figure 5:
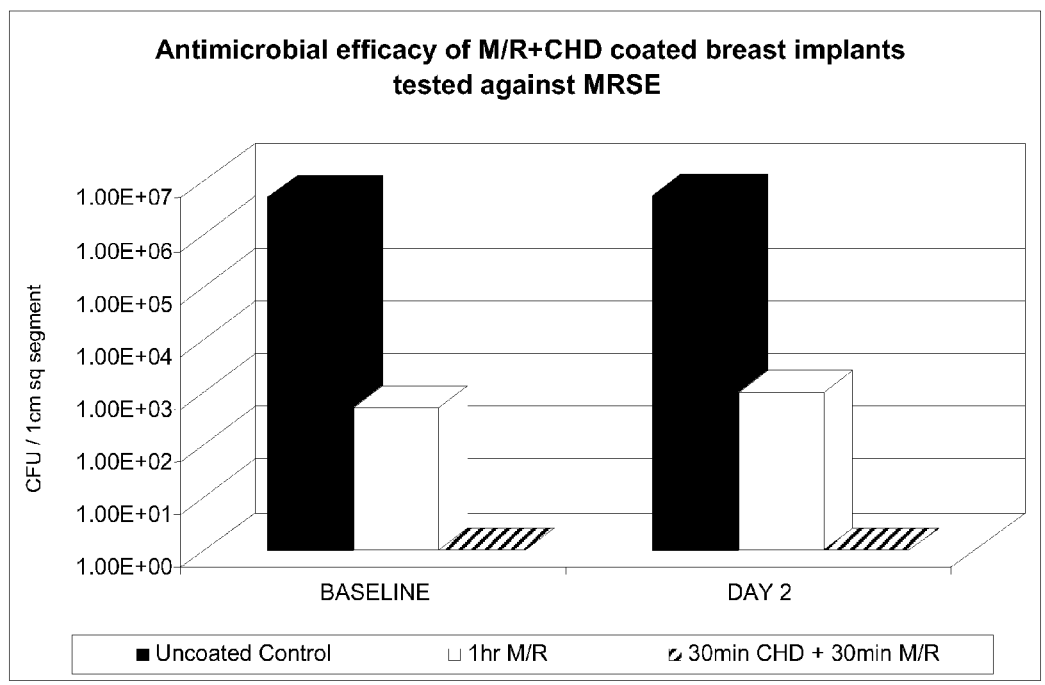
FIG. 5 illustrates the adherence of MRSE to silicone breast implants coated/impregnated with chlorhexidine diacetate and/or minocycline/rifampin.

As demonstrated, pre-treating the implant segments with the antiseptic compound (in this case, CHD) and subsequently exposing the treated segments to the antibiotic (in this case, M/R), increased antimicrobial protection is provided to the segments, when compared to the uncoated control, and a positive control immersed in the M/R solution (FIG. 5).

It is therefore intended that the foregoing detailed description be regarded as illustrative rather than limiting, and that it be understood that it is the following claims, including all equivalents, that are intended to define the spirit and scope of this invention.

The invention claimed is:

1. A method for imparting antimicrobial activity to a medical device, comprising:
  providing a solution of a first antimicrobial component, said first antimicrobial component comprising chlorhexidine;
  contacting at least a portion of the medical device with the solution of the first antimicrobial component, under conditions such that the first antimicrobial component coats or impregnates the medical device portion;
  providing a solution of a second antimicrobial component, said second antimicrobial component comprising rifampin and minocycline; and
  wherein the respective first and second antimicrobial components are sequentially coated on the medical device at a concentration effective to inhibit the adherence of bacterial and fungal organisms to the medical device.

2. The method of claim 1, wherein said first antimicrobial component is coated on the medical device first, allowed to dry and then said second antimicrobial component is coated on medical device.

3. The method of claim 1, wherein said second antimicrobial component is coated on the medical device first, allowed to dry and then said first antimicrobial component is coated on medical device.

4. The method of claim 3, wherein said solution of said second antimicrobial component includes an alkalinizing agent.

5. The method of claim 1, wherein said solution of said first antimicrobial component includes a penetrating agent.

6. The method of claim 1, wherein at least one of said solutions is heated prior to said combining step.

7. The method of claim 6, wherein each of said solutions is heated prior to said combining step.

8. The method of claim 6, wherein said at least one solution is heated to a temperature between about 30° C. and 70° C.

9. The method of claim 1, wherein the medical device is contacted with the solution of the first or second antimicrobial component for at least 30 minutes, and said contacting is carried out at a temperature between about 30° C. and 70° C.

10. The method of claim 9, wherein the medical device is contacted with the solution of the first or second antimicrobial component for at least one hour.

11. The method of claim 9, wherein the medical device is contacted with the solution of the first or second antimicrobial component for at least three hours.

* * * * *